United States Patent
Hansson

(10) Patent No.: US 11,141,203 B2
(45) Date of Patent: Oct. 12, 2021

(54) DEVICE FOR FIXATION OF BONE FRAGMENTS

(71) Applicant: SWEMAC INNOVATION AB, Linköping (SE)

(72) Inventor: Henrik Hansson, Vreta Kloster (SE)

(73) Assignee: SWEMAC INNOVATION AB, Linkoping (SE)

(*) Notice: Subject to any disclaimer, the term of this patent is extended or adjusted under 35 U.S.C. 154(b) by 239 days.

(21) Appl. No.: 15/738,596

(22) PCT Filed: Jul. 6, 2015

(86) PCT No.: PCT/SE2015/050796
§ 371 (c)(1),
(2) Date: Dec. 21, 2017

(87) PCT Pub. No.: WO2017/007382
PCT Pub. Date: Jan. 12, 2017

(65) Prior Publication Data
US 2018/0177538 A1    Jun. 28, 2018

(51) Int. Cl.
*A61B 17/74*    (2006.01)
*A61B 17/80*    (2006.01)
(Continued)

(52) U.S. Cl.
CPC ........ *A61B 17/746* (2013.01); *A61B 17/7266* (2013.01); *A61B 17/744* (2013.01);
(Continued)

(58) Field of Classification Search
CPC ..... A61B 17/74; A61B 17/742; A61B 17/744; A61B 17/746; A61B 17/748
See application file for complete search history.

(56) References Cited

U.S. PATENT DOCUMENTS 2,414,882 A * 1/1947 Longfellow ......... A61B 17/746
606/65
2,500,370 A * 3/1950 McKibbin ............ A61B 17/746
606/67
(Continued)

FOREIGN PATENT DOCUMENTS

CN    201551384    8/2010
DE    88121577    12/1988
(Continued)

*Primary Examiner* — Nicholas W Woodall
(74) *Attorney, Agent, or Firm* — Tarolli, Sundheim, Covell & Tummino LLP

(57) ABSTRACT

A device for fixation of bone fragments (4, 8) comprises a locking plate (1) for fixation on the outside of an outer bone fragment (4). The locking plate has a distal portion (1 *a*) with at least one first hole (6), extending through the locking plate, for a distal fixing means (2) and a proximal portion (1 *b*) with a second hole (7), extending through the locking plate, for a proximal fixing means (3). The locking plate (1) is configured also with a third hole (9) which is located between said at least one first hole (6) in the distal portion (1 *a*) of the locking plate and said second hole (7) in the proximal portion (1 *b*) of the locking plate and this third hole extends as the other holes through the locking plate. The device further comprises a rotary-preventing and load-carrying means (10) which is configured for inser¬tion and fixation in said third hole (9) in the locking plate (1) and by cooperating with the proximal fixing means (3) prevent rotation of the proximal fixing means but permit displa¬cement thereof in its longitudinal direction relative to the rotary-preventing and load-car¬rying means during compression after surgery of the outer and inner bone fragments (4, 8) and facilitate for the proximal fixing means to carry loading forces acting on the inner bone fragment (8).

20 Claims, 7 Drawing Sheets

(51) Int. Cl.
*A61B 17/72* (2006.01)
*A61B 17/68* (2006.01)

(52) U.S. Cl.
CPC ...... *A61B 17/8014* (2013.01); *A61B 17/8057* (2013.01); *A61B 2017/681* (2013.01)

(56) References Cited

U.S. PATENT DOCUMENTS

| | | | | |
|---|---|---|---|---|
| 2,628,614 | A * | 2/1953 | Briggs | A61B 17/746 606/67 |
| 3,791,380 | A * | 2/1974 | Dawidowski | A61B 17/746 606/68 |
| 5,041,116 | A * | 8/1991 | Wilson | A61B 17/746 606/282 |
| 8,939,978 | B2 * | 1/2015 | Watanabe | A61B 17/164 606/62 |
| 2005/0055024 | A1 | 3/2005 | James et al. | |
| 2006/0024606 | A1 | 2/2006 | Suzuki et al. | |
| 2006/0241606 | A1 | 10/2006 | Vachtenberg et al. | |
| 2007/0225714 | A1 | 9/2007 | Gradl | |
| 2007/0270847 | A1 * | 11/2007 | Shaw | A61B 17/746 606/65 |
| 2008/0057790 | A1 * | 3/2008 | Johannes | H01R 13/6625 439/620.01 |

FOREIGN PATENT DOCUMENTS

| | | |
|---|---|---|
| GB | 1069670 | 5/1967 |
| JP | 03158150 | 7/1991 |
| JP | 2010259823 | 11/2010 |
| JP | 2010534106 | 11/2010 |
| WO | 2007054591 | 5/2007 |
| WO | 2013151501 | 10/2013 |

* cited by examiner

DEVICE FOR FIXATION OF BONE FRAGMENTS

RELATED APPLICATIONS

This application corresponds to PCT/SE2015/050796, filed Jul. 6, 2015, the subject matter, of which is incorporated herein by reference in its entirety.

TECHNICAL FIELD

The present invention relates to a device for fixation of bone fragments at proximal thigh-bone or femoral fractures, generally known also as hip fractures. To this end, the device comprises a locking plate for fixation on the outside of an outer bone fragment. The locking plate has a distal portion with at least one first hole, extending through the locking plate, for a distal fixing means and a proximal portion with a second hole, extending through the locking plate, for a proximal fixing means. The device further comprises at least one distal fixing means. This distal fixing means is configured for insertion and fixation of the fixing means in said at least one first hole in the distal portion of the locking plate and fixation of the fixing means in the outer bone fragment. The device also comprises a proximal fixing means. The proximal fixing means is configured with a first fixing portion for fixation of the fixing means in an inner bone fragment. The proximal fixing means is also configured with a second fixing portion for insertion of the fixing means in said second hole in the proximal portion of the locking plate for connection of the fixation means to the locking plate for primary compression of the outer and inner bone fragments. The proximal fixing means is further configured with a middle portion which is situated between the first and second fixing portions. This middle portion is configured to extend through the outer bone fragment and to permit, during secondary compression of the outer and inner bone fragments, displacement of the outer bone fragment and the proximal fixing means relative to each other, whereby the connection of the fixing means to the locking plate for achieving primary compression ceases.

BACKGROUND OF THE INVENTION

Devices of the abovementioned type exist in a large number of embodiments. A device comprising the abovementioned locking plate as well as distal and proximal fixing means is found in a system provided by applicant and referred to by applicant as the "SWEMAC CHS Compression Hip Screw System". The system constitutes a simple and easy to use solution to surgeons having the task to reduce and stabilize a hip fracture. The locking plate in the system is proximally provided with a sleeve which is made in one piece with the locking plate. The sleeve which in the longitudinal direction of the locking plate extends at an angle relative to said locking plate, can be located in an outer bone fragment in the form of e.g. the thighbone or femur and has a through-hole in the longitudinal direction of the sleeve for a proximal fixing means in the form of a lag screw which is configured for fixation in an inner bone fragment in the form of e.g. the femoral head. The sleeve is intended to, inter alia, carry loading forces acting on particularly the femoral head after surgery. Particularly when the patient during rehabilitation begins to walk around and subject the leg to loads, but also due to influences from the muscles while the patient is still lying in bed. The sleeve of the locking plate and the associated lag screw are rather voluminous and much bone tissue has to be removed to permit location of the lag screw and the sleeve of the locking plate in the femur. The sleeve of the locking plate may e.g. have a diameter of about 13 mm and the lag screw a diameter of about 11 mm. If too much bone tissue is removed, the cooperation between the bone and the implant may be negatively affected. A compression screw can be used to compress the fracture. The compression screw is then screwed into the lag screw in the proximal hole in the locking plate until it engages the locking plate, whereupon continued screwing of the compression screw into the lag screw at the same time said compression screw still engages the locking plate, generates a pulling force on the lag screw towards the locking plate and presses the locking plate harder against the outer bone fragment such that the bone fragments are drawn towards each other. The sleeve is at the exit end configured with two flat edges and the lag screw has surfaces fitting therewith, whereby the lag screw is prevented from rotation.

Bone nails of the type comprising a sleeve with a lateral opening in a front end portion of the sleeve and at least one pin which is displaceably mounted inside said sleeve and has at least one front end portion which defines the first fixing portion of the proximal fixing means and which during displacement of the pin and simultaneous deformation of said at least one front end portion is driven out of the sleeve via the lateral opening therein for engagement in the surrounding bone tissue in the inner bone fragment, can not be used at the abovementioned prior art device. Use thereof should namely lead to that the sleeve of the locking plate must be given even larger dimensions than what is now common, with the risk that too much bone tissue for safe fixation has to be removed, alternatively that the proximal fixing means must be made smaller, which reduces the fixing capacity thereof.

SUMMARY OF THE INVENTION

The object of the present invention is therefore to provide a device as defined above and with an improved ability to carry loading forces acting on the inner bone fragment.

Another object of the present invention is to provide a device which requires removal of bone tissue to a smaller extent compared to if a locking plate with a sleeve is used. This also provides for a better fixation of the device to the bone. Alternatively, proximal fixing means of larger dimensions can be used.

A still further object of the present invention is to configure the device for preventing rotation of the proximal fixing means after fixation thereof in the inner bone fragment, such that said fixing means can not be unscrewed.

The above objects are achieved by configuring the locking plate of the device according to the present invention also with a third hole which is located between said at least one first hole in the distal portion of the locking plate and said second hole in the proximal portion of the locking plate and this third hole extends as the other holes through the locking plate. Additionally, the device according to the present invention comprises a rotary-preventing and load-carrying means which is configured for insertion and fixation in said third hole in the locking plate and by cooperating with the proximal fixing means prevent rotation of the proximal fixing means but permit displacement thereof in its longitudinal direction relative to the rotary-preventing and load-carrying means during secondary compression of the outer and inner bone fragments and facilitate for the proximal fixing means to carry loading forces acting on the inner bone fragment.

Thus, except for getting a device which fulfils the above objects and having the abovementioned advantages and improvements relative to e.g. the abovementioned prior art device with a locking plate which comprises a sleeve for a proximal fixing means in the form of a lag screw, the present device permits use of proximal fixing means in the form of e.g. a sleeve with at least one lateral opening in a front end portion of said sleeve and at least one inside said sleeve displaceably mounted pin with a front end portion which during displacement of the pin and simultaneous deformation of said at least one front end portion is driven out of the sleeve via the lateral opening therein. The device according to the present invention is also easier to manufacture inter alia while the locking plate does not need to be configured with a sleeve and is therefore also not so expensive.

Another advantage is that except for the locking plate, other components in e.g. the abovementioned "SWEMAC CHS Compression Hip Screw System" may if desired be used also in the device according to the present invention.

BRIEF DESCRIPTION OF THE DRAWINGS

The above-mentioned and additional features of preferred embodiments of the present invention and the advantages therewith will be further described below with reference to the accompanying drawings. In the drawings.

DETAILED DESCRIPTION OF PREFERRED EMBODIMENTS

Figure 1:
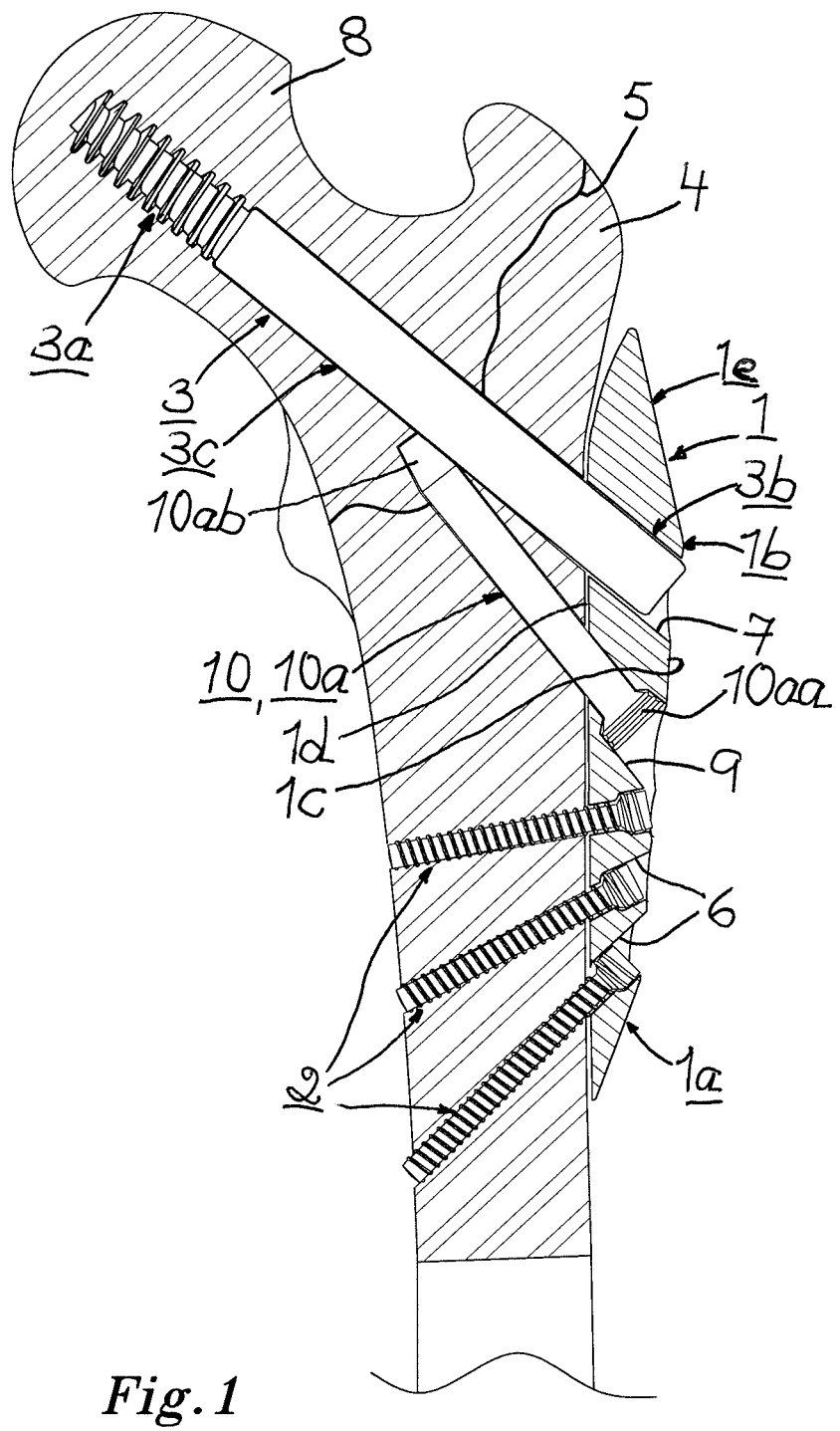
FIG. 1 is a schematic sectional view through upper parts of a thighbone or femur, including the femoral shaft and the femoral head, and a partly sectional view of a first embodiment of the device according to the present invention, with a proximal fixing means in the form of a bone screw and a first embodiment of the rotary-preventing and load-carrying means.

The present invention relates to a device for fixation of bone fragments at proximal thigh-bone or femoral fractures, generally known also as hip fractures, e.g. femoral shaft fractures, stable trochanteric hip fractures and unstable trochanteric hip fractures. The device comprises, as in prior art embodiments for the same purpose, a locking plate 1, at least one, in the illustrated embodiments three distal fixing means 2 and a proximal fixing means 3. The locking plate 1 is configured for fixation on the outside of an outer bone fragment 4, on one side of a fracture 5. In the illustrated embodiments, the locking plate 1 is attached to the proximal part of a thighbone or femur 4. The locking plate 1 comprises a distal portion 1a with at least one first, in the illustrated embodiments three first holes 6 extending through the locking plate and provided for the distal fixing means 2. The locking plate 1 further comprises a proximal portion 1b with a second hole 7 extending through the locking plate and provided for the proximal fixing means 3. The distal fixing means 2 are each configured for insertion and fixation thereof in one of said holes 6 in the distal portion 1a of the locking plate 1 and for fixation of the fixing means in the outer bone fragment 4. The distal fixing means 2 can be configured as e.g. locking or non-locking cortical bone screws. The proximal fixing means 3 is configured with a first fixing portion 3a for fixation of the fixing means in an inner bone fragment 8 on the opposite side of the fracture 5. In the illustrated embodiments, the first fixing portion 3a of the proximal fixing means 3 is fixed or locked in an inner bone fragment in the form of the femoral head 8. The proximal fixing means 3 is also configured with a second fixing portion 3b for insertion of the fixing means in said second hole 7 in the proximal portion 1b of the locking plate 1 for connection of the fixing means to the locking plate for primary compression of the outer and inner bone fragments, i.e. the proximal fixing means is connected to the locking plate in a suitable manner to permit, during surgery, compression of the bone fragments 4, 8 for stabilization of the fracture 5 after possible correction, reduction, of the fracture by pressing the locking plate by means of the proximal fixing means against the outer bone fragment and thereby, the outer bone fragment against the inner bone fragment. In the drawings, the fracture 5 is reduced alternatively has from the beginning been without dislocation. The proximal fixing means 3 is also configured with a middle portion 3c located between the first and second fixing portions 3a, 3b. This middle portion 3c is configured to extend through the outer bone fragment 4 and, during secondary compression of the outer and inner bone fragments 4, 8, i.e. during compression of the bone fragments after surgery, when due to influences from the muscles while the patient is still lying in bed and particularly when the patient during rehabilitation begins to walk around and subject the leg to loads and the bone fragments because of resorption of dead bone tissue and the space between the bone fragments generated thereby, due to the load strives to move towards each other, to permit displacement of the outer bone fragment 4 and the proximal fixing means 3 relative to each other. Hereby, the connection of the proximal fixing means 3 to the locking plate 1 in order to achieve the primary compression ceases, since the locking plate through the distal fixing means 2 is locked to the outer bone fragment 4 and since the proximal fixing means 3 is locked to the inner bone fragment 8 and extends through the locking plate. Despite the dynamization and the displacement of the proximal fixing means 3 relative to the locking plate 1, a certain stability in the device and thereby, of the fracture is maintained.

In order to not only maintain stability in the device and of the fracture, but also, as mentioned above, improve it by better take up and carry loading forces acting on the inner bone fragment 8, provide for less removal of bone tissue for the location of members of the device in the bone fragments and configuring the device to prevent rotation of the proximal fixing means 3 after fixation thereof in the inner bone fragment such that said fixing means can not be unscrewed, the locking plate 1 for the device according to the present invention is configured also with a third hole 9 which is located between the first holes 6 in the distal portion 1a of the locking plate and the second hole 7 in the proximal portion 1b of the locking plate. The third hole 9 extends as the other holes 6, 7 through the locking plate. For the abovementioned purposes, the device according to the present invention also comprises a rotary-preventing and load-carrying means 10 which is configured for insertion and fixation in said third hole 9 in the locking plate 1. By cooperating with the proximal fixing means 3, the rotary-preventing and load-carrying means 10 prevents rotation of the proximal fixing means but permits at the same time displacement of said fixing means in its longitudinal direction relative to the rotary-preventing and load-carrying means during secondary compression of the outer and inner bone fragments 4, 8. The rotary-preventing and load-carrying means 10 further facilitates for the proximal fixing means 3 to carry loading forces acting on the inner bone fragment 8 by supporting said fixing means through its cooperation therewith. The cooperation between the rotary-preventing and load-carrying means 10 and the proximal fixing means 3 in order to prevent said rotation of the proximal fixing means but permit displacement thereof in its longitudinal direction, can be established in different ways. Improved uptaking or carrying of loading forces on the inner bone fragment 8 can be accomplished e.g. by moving said cooperation between the rotary-preventing and load-carrying means 10 and the proximal fixing means 3 farther in towards the inner bone fragment than what is possible with a locking plate with a sleeve according to prior art, e.g. by making the rotary-preventing and load-carrying means sufficiently long. A length of between about 20 mm and about 75 mm has been found to be suitable, but the length can of course be larger as well as smaller. The diameter of the rotary-preventing and load-carrying means 10 can be between about 4 mm and 8 mm, e.g. about 6 mm, but may be smaller as well as larger, under all circumstances however, substantially smaller than the 13 mm the diameter of the sleeves of prior art locking plates normally amount to.

In other words, one can summarize the present invention as that the sleeve for the proximal fixing means of the locking plate in prior art devices is replaced by a separate rotary-preventing and load-carrying means which is located in the locking plate, i.e. is replaced by a means which functions as the sleeve, but which improves these functions and additionally permits use of other types of proximal fixing means than bone or lag screws and simplifies and reduces the costs for manufacturing the device.

Figure 2:
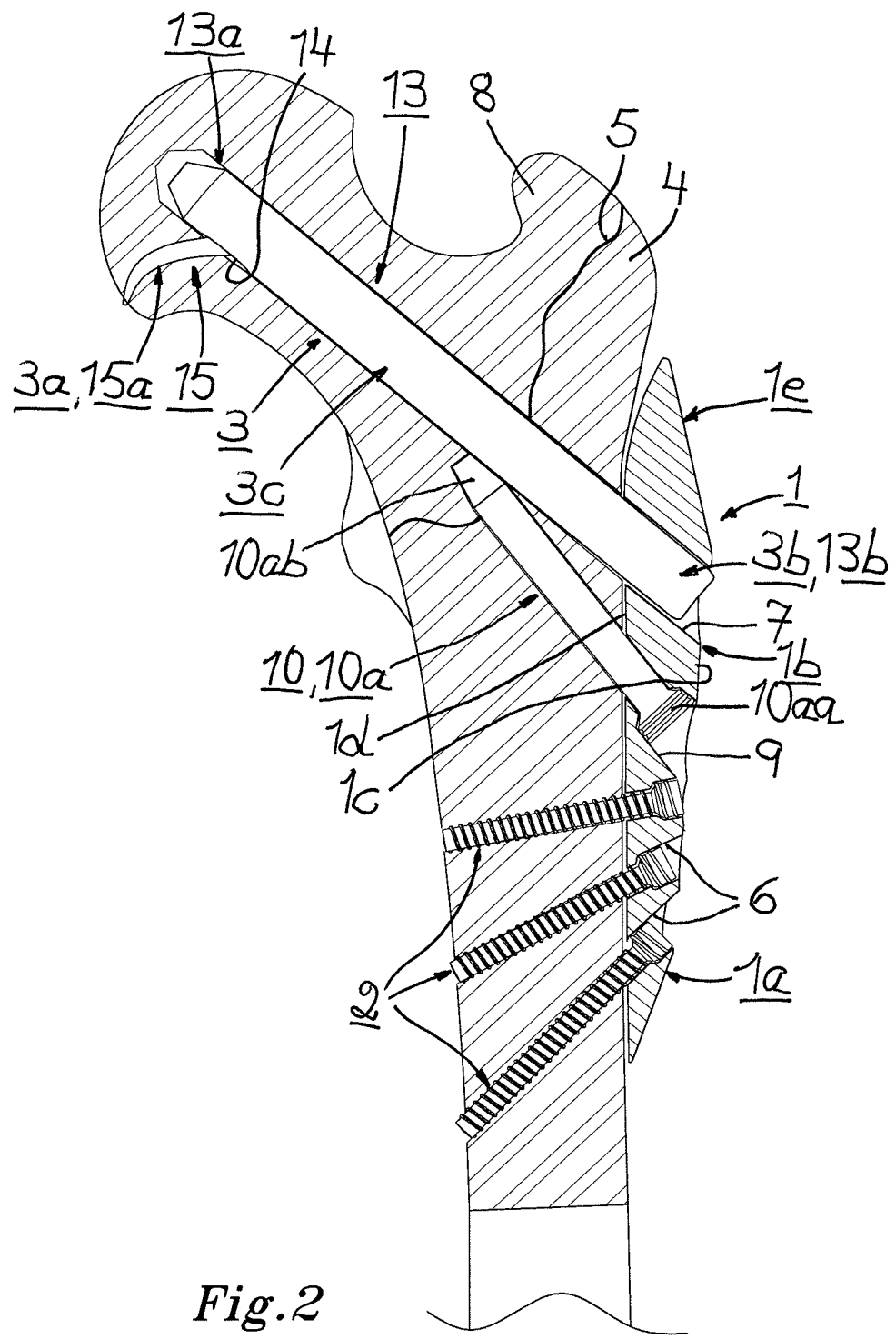
FIG. 2 is a schematic sectional view similar to FIG. 1 and a partly sectional view of a second embodiment of the device according to the present invention, with a proximal fixing means in the form of a bone nail and the first embodiment of the rotary-preventing and load-carrying means.
Figure 3:
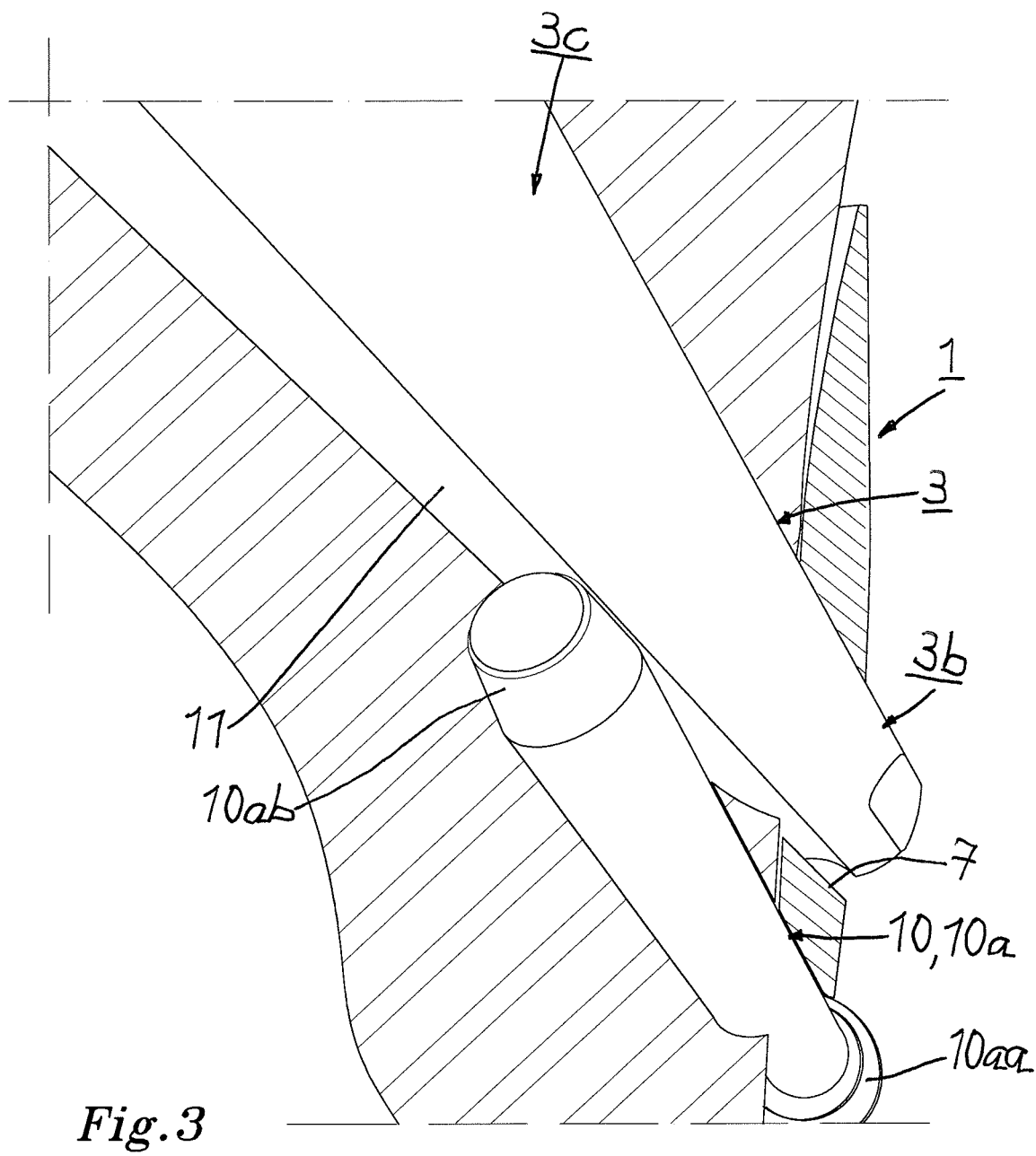
FIG. 3 illustrates with an enlarged schematic view details of the first embodiment of the rotary-preventing and load-carrying means.

In order to attain optimum cooperation between the rotary-preventing and load-carrying means 10 and the proximal fixing means 3, the third hole 9 in the locking plate 1 for the rotary-preventing and load-carrying means is in the first and second embodiments of the device according to the present invention illustrated in FIGS. 1 and 2, and seen in the cross-direction of the locking plate, configured to run at an angle relative to the second hole 7 in the locking plate for the proximal fixing means. When the respective means 3, 10 are inserted or introduced into their respective holes 7, 9, the angle is such that the rotary-preventing and load-carrying means 10 is directed towards the proximal fixing means 3. This angle can e.g. as in the illustrated embodiments according to FIGS. 1 and 2 be about 15°. The rotary-preventing and load-carrying means 10 is in the illustrated embodiments according to FIGS. 1 and 2 configured as a long and narrow rod 10a, in the following referred to a "peg" with a threaded rear end portion 10aa for fixation in the third hole 9 in the locking plate 1. The front end portion 10ab of the peg 10a is in the illustrated embodiments conically shaped for optimum engagement in a longitudinal groove 11 in the proximal fixing means 3. Thus, the groove 11 has, in the illustrated embodiments, a substantially round shape corresponding to the round shape of the conical front end portion 10ab of the peg 10a. The front end portion of the peg may alternatively have edges and be tapering and engage a longitudinal groove with edges in the proximal fixing means. Also, the angle between the rotary-preventing and load-carrying means 10 and the proximal fixing means 3 is with preference such that the point of engagement of the front end portion 10ab of the peg 10a in the groove 11 in the proximal fixing means is situated relatively far into the femur, whereby as mentioned the uptaking of loading forces acting on the inner bone fragment 8 is improved compared to prior art devices. Advantageously, the angle is such that the peg 10a in its longitudinal direction also lies substantially in line with or at least in parallel with the loading forces acting on the inner bone fragment 8. The conicity of the front end portion 10ab of the peg 10a is such that the part of the conical surface that engages the groove runs in parallel with the surface of the groove, which also improves the engagement of the proximal fixing means 3 and thereby the uptaking capacity of the loading forces acting on the inner bone fragment 8 (see FIG. 3). Since the front end portion 10ab of the rotary-preventing and load-carrying means 10 having the shape of a peg 10a engage the groove 11 in the proximal fixing means 3, said proximal fixing means is effectively prevented from rotating about its longitudinal axis. The groove 11 in the proximal fixing means 3 is in the illustrated embodiments according to FIGS. 1 and 2 configured to extend, from the second fixing portion 3b of the proximal fixing means, along at least a part of the middle portion 3c of said fixing means. In FIG. 3 the groove 11 is clearly shown. The length of the peg 10a may, as mentioned, vary as desired. It is e.g. also possible to configure the peg 10a with such length that if the peg is screwed sufficiently far into said third hole 9 therefor, it can be brought to engage the proximal fixing means 3 with such force that it locks said fixing means to such extent that compression is permitted only in the longitudinal direction of the locking plate. By configuring the peg 10a with such length that it together with the proximal fixing means 3 extends through the fracture, rotary stability is obtained in the fracture. Consequently, the peg 10a has a length of between about 25 mm and about 75 mm, preferably, as in the illustrated embodiments, a length of about 50 mm, but the length can of course be larger as well as smaller.

Figure 4:
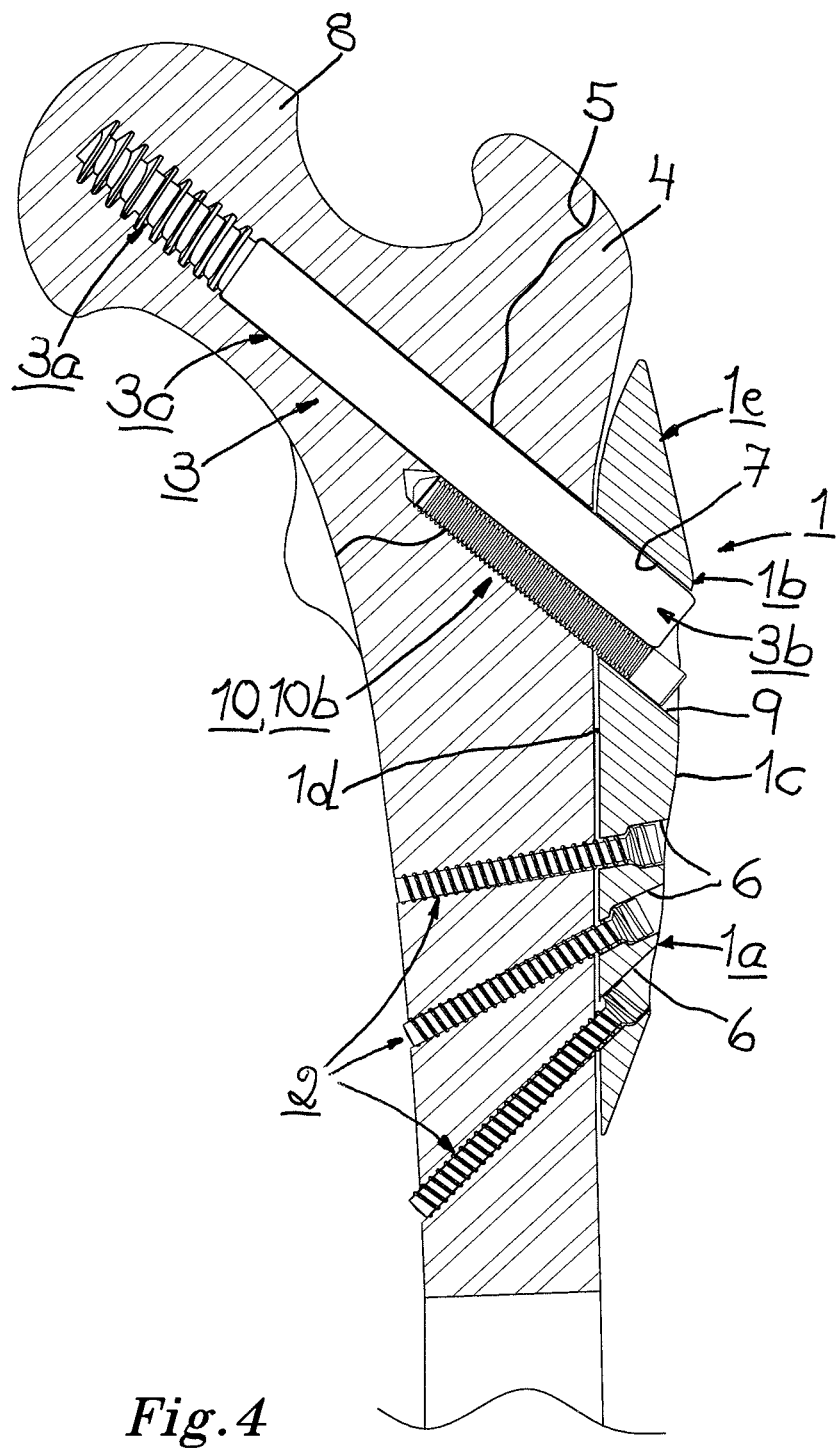
FIG. 4 is a schematic sectional view similar to FIG. 1 and a partly sectional view of a third embodiment of the device according to the present invention, with a proximal fixing means in the form of a bone screw and a second embodiment of the rotary-preventing and load-carrying means.
Figure 5:
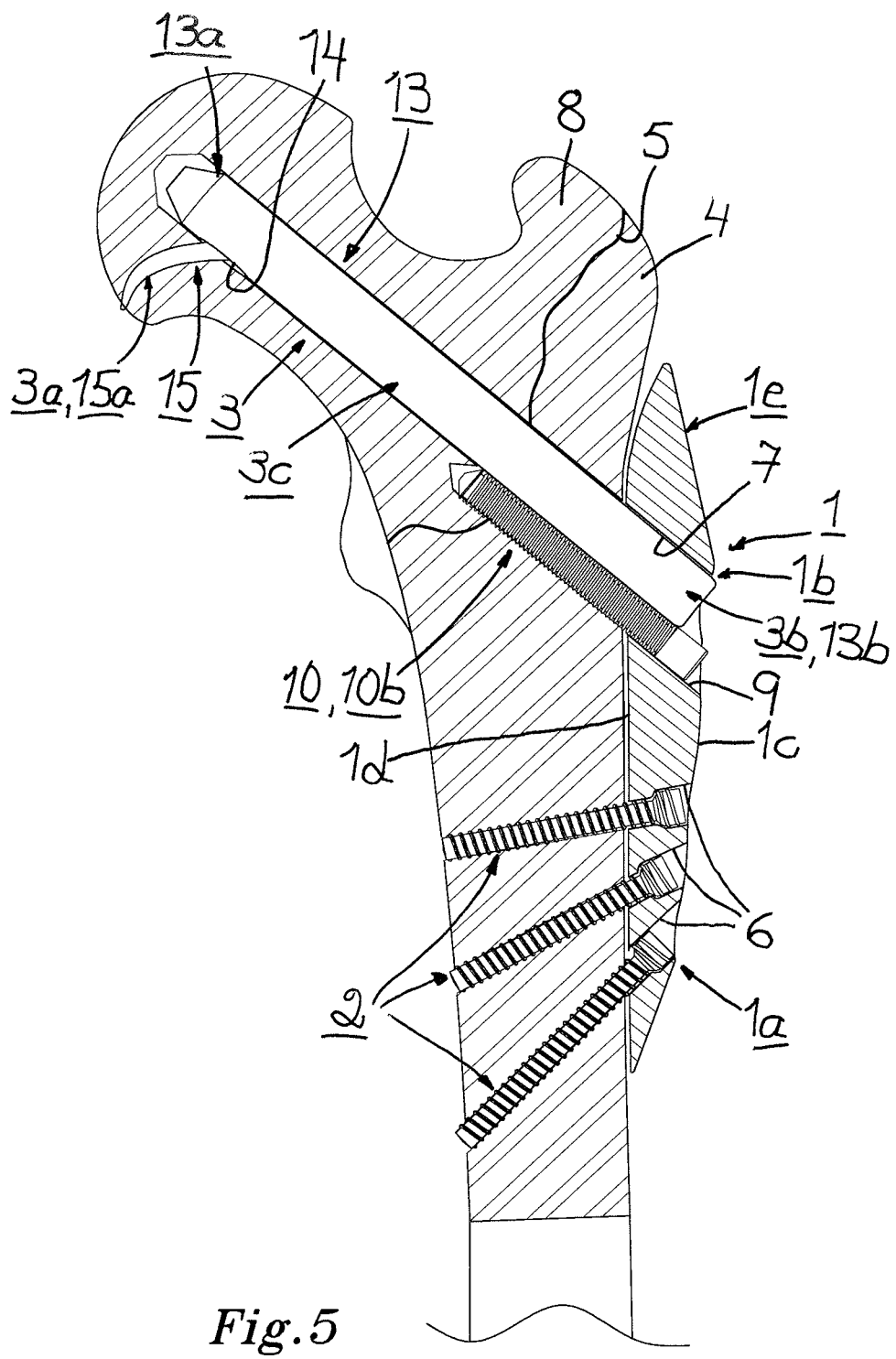
FIG. 5 is a schematic sectional view similar to FIG. 1 and a partly sectional view of a fourth embodiment of the device according to the present invention, with a proximal fixing means in the form of a bone nail and the second embodiment of the rotary-preventing and load-carrying means.
Figure 6:
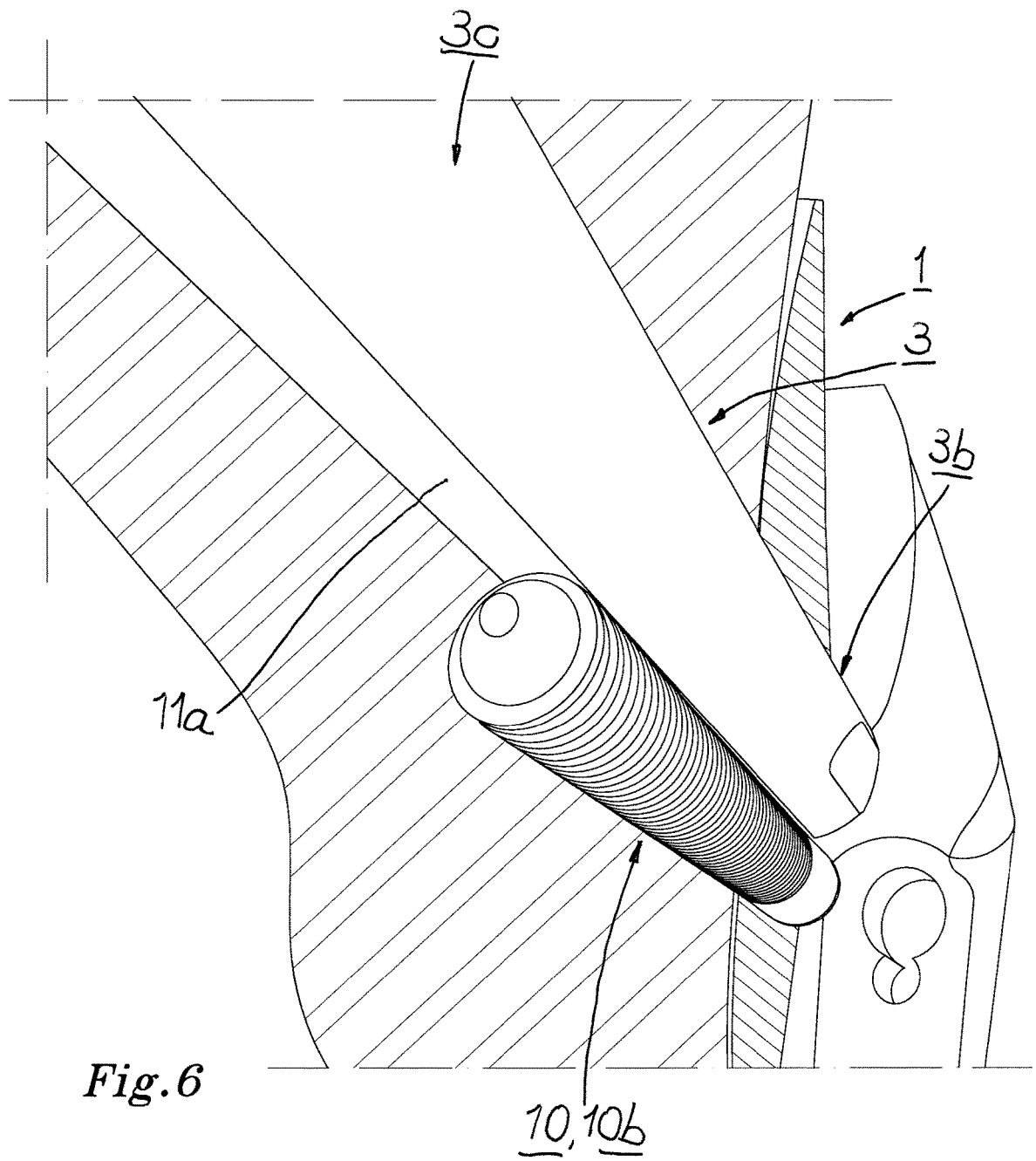
FIG. 6 illustrates with an enlarged schematic view details of the second embodiment of the rotary-preventing and load-carrying means.

In order also to attain effective cooperation between the rotary-preventing and load-carrying means 10 and the proximal fixing means 3, the third hole 9 in the locking plate 1 for the rotary-preventing and load-carrying means is in the third and fourth embodiments of the device according to the present invention illustrated in FIGS. 4 and 5, seen in the cross-direction of the locking plate, configured to run in parallel with the second hole 7 in the locking plate for the proximal fixing means 3. Thus, when the respective means 3, 10 are inserted or introduced into their respective holes 7, 9, the rotary-preventing and load-carrying means runs in parallel with the proximal fixing means. The rotary-preventing and load-carrying means 10 is in the illustrated embodiments according to FIGS. 4 and 5 configured as a screw 10b for fixation in the third hole 9 in the locking plate 1. The screw 10b is in the illustrated embodiments threaded along almost its entire length. The screw 10b is in its longitudinal direction engaging a correspondingly shaped longitudinal groove 11a in the proximal fixing means 3. The groove 11a has a corresponding shape but not a corresponding length as the groove 11 in the abovementioned embodiments according to FIGS. 1 and 2. The groove 11a is in the embodiments of FIGS. 4 and 5 namely longer and does not extend only along a part of the middle portion 3c of the proximal fixing means 3, but also along the second fixing portion 3b thereof, i.e. the groove 11a opens at the back of the proximal fixing means. Since the screw 10b engages the groove 11a in the proximal fixing means 3, said fixing means is effectively prevented from rotating about its longitudinal axis and the uptaking or carrying of loading forces acting on the inner bone fragment 8 occurs in substantially the entire longitudinal direction of the screw-like rotary-preventing and load-carrying means 10 (see FIG. 6). Since the screw 10b engages the groove 11a in the proximal fixing means 3, the parallel holes 7, 9 for the proximal fixing means 3 and the screw-like rotary-preventing and load-carrying means 10 respectively, are also configured such that they peripherally to a certain extent intersect each other. By configuring the screw 10b with such length that it together with the proximal fixing means 3 extends through the fracture, rotary stability is obtained in the fracture. Consequently, the screw 10b has a length of between about 20 mm and about 70 mm, preferably, as in the illustrated embodiments, a length of about 45 mm, but the length can of course be larger as well as smaller.

Alternative embodiments of the rotary-preventing and load-carrying means 10 are possible as long as it fulfills the functional demands put thereon according to the present invention.

In order to achieve optimum effect from the ability of the rotary-preventing and load-carrying means 10 to uptake or carry loading forces acting on the inner bone fragment 8, the second hole 7 in the proximal portion 1b of the locking plate 1 and the third hole 9 in the locking plate for the rotary-preventing and load-carrying means are located in one and the same plane as seen in the longitudinal direction of the locking plate, i.e. the rotary-preventing and load-carrying means 10 is located substantially right under the proximal fixing means if seen from above in the longitudinal direction of the locking plate. Loading forces acting on the inner bone fragment 8 when the patient is up walking around, which from above affect the fracture 5 and the device according to the invention, are effectively carried. For the same purpose, said plane extends, seen in the longitudinal direction of the locking plate 1, substantially right through the locking plate from its insertion side 1c for the fixing means 2, 3 and for the rotary-preventing and load-carrying means 10 to the side 1d of the locking plate which engages the outer bone fragment 4.

In order to achieve best possible fixation of the locking plate in the outer bone fragment 4, the third hole 9 for the rotary-preventing and load-carrying means 10 in the locking plate is, seen in the cross direction of the locking plate, configured to run at an angle relative to the first hole or holes 6 for the distal fixing means 2 in the distal portion 1a of the locking plate. The first holes 6, which when as illustrated the locking plate 1 is configured with two or more such holes, can in turn extend in parallel with each other if seen in the cross-direction of the locking plate or alternatively, as in the illustrated embodiments, run at an angle relative to each other in order to further improve the fixation of the locking plate in the outer bone fragment, and then they also extend at an angle relative to the second hole 7 in the proximal portion 1b of the locking plate 1 and relative to the third hole 9 for the rotary-preventing and load-carrying means 10.

The first hole or holes 6 in the distal portion 1a of the locking plate 1, the second hole 7 in the proximal portion 1b of the locking plate and the third hole 9 in the locking plate extend in more detail all, seen in the cross direction of the locking plate, obliquely through the locking plate such that distal fixing means 2 which have been inserted into said first hole or holes extend in the direction of insertion away from the proximal fixing means 3 which has been inserted into said second hole and away from the rotary-preventing and load-carrying means 10 which has been inserted into said third hole. In other words, this means that the distal fixing means is/are angled such that they run obliquely in distal direction, while the proximal fixing means and the rotary-preventing and load-carrying means run obliquely in proximal direction. This and the fact that in the illustrated embodiments, the first holes 6 in the distal portion 1a of the locking plate 1, the second hole 7 in the proximal portion 1b of the locking plate and the third hole 9 in the locking plate all extend, seen in the cross-direction of the locking plate, obliquely through the locking plate, such that distal fixing means 2 which have been inserted into said first hole or holes are located in planes which cross each other on the insertion side 1c of the locking plate and cross the planes in which the proximal fixing means 3 which has been inserted into the second hole and in which the rotary-preventing and load-carrying means 10 which has been inserted into the third hole are located, means that the operation wound or incision which has to be made for implanting the device according to the present invention in correct position at the outer bone fragment can be minimized. From where said planes cross each other, the various means 2, 3, 10 are easy to position in the respective holes 6, 7, 9 therefor in the locking plate 1.

Also since the first holes 6 for the distal fixing means 2 in the distal portion 1a of the locking plate 1 extend, seen in the longitudinal direction of the locking plate, at an angle relative to each other and at an angle relative to the plane through the second hole 7 in the proximal portion 1b of the locking plate and through the third hole 9 for the rotary-preventing and load-carrying means 10 in the locking plate, fixation of the locking plate to the outer bone fragment 4 is improved.

Since in the illustrated embodiments the first holes 6 in the distal portion 1a of the locking plate 1 to a certain extent run, seen in the longitudinal direction of the locking plate, obliquely through the locking plate such that distal fixing means 2 which have been inserted into the first holes are located in planes which cross each other on the insertion side 1c of the locking plate and cross the plane in which the proximal fixing means 3 which has been inserted into the second hole 7 and in which the rotary-preventing and load-carrying means 10 which has been inserted into the third hole 9 are located, it is also hereby achieved an effective fixation of the locking plate 1 in the outer bone fragment 4. From where said planes cross each other, the various means 2, 3, 10 are also here easy to position in the respective holes 6, 7, 9 therefor in the locking plate 1.

Figure 7:
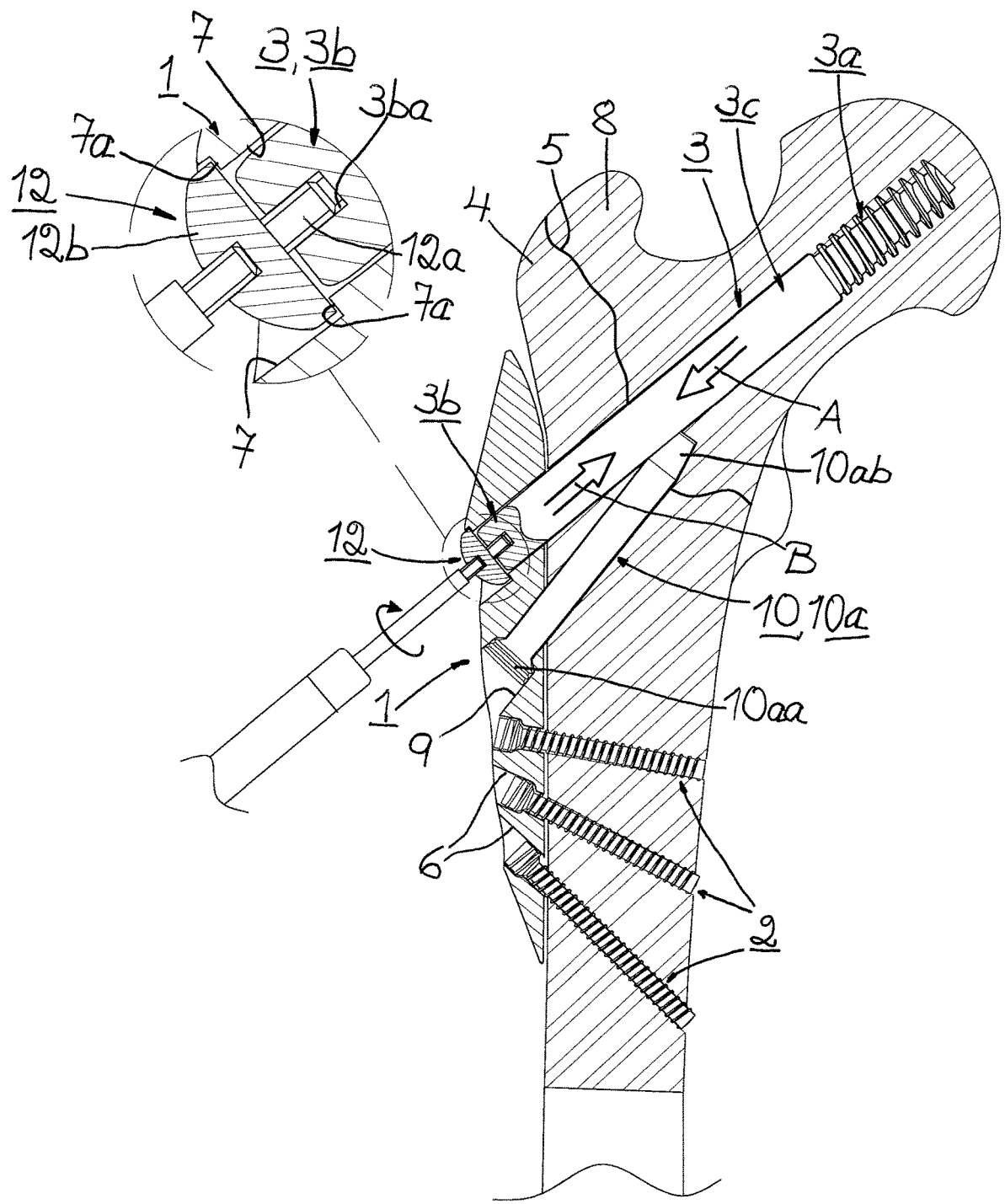
FIG. 7 illustrates with a schematic sectional view how a proximal fixing means can be attached to a locking plate by means of a compression screw.

As is apparent from FIG. 7, the second fixing portion 3b of the proximal fixing means 3 is configured with a threaded recess 3ba for a locking and compression screw 12 for connection of the proximal fixing means to the locking plate 1. The screw shaft 12a of the locking and compression screw 12 can then be screwed into the proximal fixing means 3 in the proximal hole 7 in the locking plate 1 until the screw head 12b engages an engagement surface 7a in and/or at the hole 7 for the proximal fixing means in the locking plate and bottoms in the recess 3ba in the second fixing portion 3b of the proximal fixing means 3. The locking and compression screw 12 shall then preferably be located substantially inside the hole 7 and not protrude from the locking plate 1 to a larger extent. Continued rotation of the locking and compression screw 12 in the proximal fixing means while said locking and compression screw at the same time still engages the locking plate 1, causes rotation of the proximal fixing means 3 and brings the first fixing portion 3a thereof, when said portion has the shape of a thread, to screw itself further into the inner bone fragment 8 and thereby generate a pulling force (see arrow A in FIG. 7) on said inner bone fragment such that it is pulled towards the outer bone fragment 4 for primary compression of said bone fragments after the locking plate has come to engage the outer side of the outer bone fragment or alternatively, since the locking plate already engages the outer bone fragment and is pressed against it. With advantage, you can hereby first drill a hole (not shown) for the proximal fixing means 3 which is e.g. about 5 mm longer than the proximal fixing means is screwed into the inner bone fragment 8. In this embodiment, the rotary-preventing and load-carrying means 10 may not be arranged prior to the compression of the bone fragments, since this will prevent the proximal fixing means 3 from screwing itself further into the inner bone fragment.

A possible alternative (not shown) can be that one again screws the locking and compression screw 12 into the proximal fixing means 3 in the proximal hole 7 in the locking plate 1 until it engages the engagement surface 7a in and/or at the hole 7 for the proximal fixing means in the locking plate but without it bottoming in the recess 3ba in the second fixing portion 3b of the proximal fixing means 3. The locking and compression screw 12 shall then preferably be located substantially inside the hole 7 and not protrude from the locking plate 1 to a larger extent. Continued rotation of the locking and compression screw 12 in the proximal fixing means while said locking and compression screw at the same time still engages the locking plate 1, generates a pulling force on the proximal fixing means (which can be locked against rotation or at least preferably does not rotate) and thereby on the inner bone fragment in the direction towards the locking plate, retains the proximal fixing means against the locking plate and also presses the locking plate harder against the outer bone fragment 4 such that the bone fragments 4, 8 are moved towards each other (see arrows A and B in FIG. 7) for primary compression thereof. This alternative embodiment is perfectly suitable also for proximal fixing means having a first fixing portion of another type than a thread. In this embodiment, the rotary-preventing and load-carrying means 10 can be arranged also prior to the compression of the bone fragments.

In order to obtain an optimally adapted positioning of the locking plate 1 at the outer bone fragment 4, in the illustrated embodiments the femur, and prevent medial displacement thereof (the outer bone fragment 4) relative to the femoral neck and the femoral head (the inner bone fragment 8) at the same time a dynamic axial compression of the bone fragments 4, 8 is permitted, the locking plate 1 comprises a lateral support 1e proximally of the proximal portion 1b thereof. In the illustrated embodiments, the lateral support 1e is configured in one piece with the rest of the locking plate 1, but it can alternatively be a separate member which in any suitable manner is connected to the locking plate.

Alternatively, the locking plate 1 may distally also be configured with displaceable lateral plates (not shown) in order to, as required, increase or reduce the length of the implant. These lateral plates can then with advantage be configured e.g. with rails which engage recesses in the locking plate 1 or the opposite be configured with recesses for engagement therein of rails on the locking plate. The lateral plates are then also provided with said first holes 6 for the distal fixing means 2. While the width of the locking plate 1 to a certain extent increases thanks to the lateral plates, the first holes 6 for the distal fixing means 2 can be configured to run obliquely through the lateral plates, seen in their longitudinal direction, to a higher degree than in the embodiment without lateral plates and then with advantage so, that the distal fixing means 2 which are inserted into the first holes are located in planes which cross each other on that side 1d of the locking plate which engages the outer bone fragment 4. Of course, the first holes 6 for the distal fixing means 2 are here also configured to run at an angle relative to the plane through the second hole 7 in the proximal portion 1b of the locking plate and through the third hole 9 for the rotary-preventing and load-carrying means 10, seen in the longitudinal direction of the locking plate 1, and of course, the first holes for the distal fixing means are also configured to run in parallel or at an angle relative to each other and at an angle relative to the second hole in the proximal portion of the locking plate and relative to the third hole for the rotary-preventing and load-carrying means seen also in the cross direction of the locking plate 1. The lateral plates may also have different lengths.

As is apparent from the drawings, the proximal fixing means 3 can be configured in different ways. It may e.g., as illustrated in FIGS. 1 and 4, be configured as a bone screw, whereby the bone screw as indicated above on the outer side thereof is provided with at least one groove 11 or 11a which runs in the longitudinal direction of the bone screw for engagement in the groove by the rotary-preventing and load-carrying means 10. Alternatively, the bone screw may be configured with two or more grooves 11 or 11a for engagement in one of the grooves by the rotary-preventing and load-carrying means 10. With several grooves 11 or 11a it is possible to avoid that the bone screw is screwed too far into the inner bone fragment 8 before the groove is correctly located relative to the rotary-preventing and load-carrying means 10.

The proximal fixing means 3 can alternatively, as is apparent from FIGS. 2 and 5, be configured as a bone nail. In the illustrated embodiments, the bone nail comprises a sleeve 13 with at least one lateral opening 14 in a front end portion 13a of the sleeve and at least one pin 15 which is displaceably mounted inside said sleeve and has at least one front end portion 15a which defines the first fixing portion 3a of the proximal fixing means 3 and which during displacement of the pin and simultaneous deformation of said at least one front end portion is driven out of the sleeve via the lateral opening therein for engagement in the surrounding bone tissue in the inner bone fragment 8. Displacement of the pin 15 is performed from the rear end portion 13a of the sleeve 13, which to this end is configured in a manner known per se while the sleeve at the same time is provided with a recess for a locking and compression screw. Similar to the abovementioned bone screw, the bone nail is on the outer side thereof provided with at least one groove 11 or 11a which runs in the longitudinal direction of the bone screw for engagement in the groove by the rotary-preventing and load-carrying means 10. In the illustrated embodiments according to FIGS. 2 and 5, the sleeve 13 of the bone nail is on the outer side thereof and in line with the lateral opening 14 provided with one groove 11 or 11a which runs in the longitudinal direction of the sleeve for engagement in the groove by the rotary-preventing and load-carrying means 10. Hereby, one know, when the groove is correctly located relative to the rotary-preventing and load-carrying means 10, where the front end portion 15a of the pin 15 will protrude from the lateral opening 14 in the sleeve 13 and into surrounding bone tissue in the inner bone fragment 8. Alternatively, the sleeve 13 of the bone nail may be configured with two or more grooves 11 or 11a for engagement in one of the grooves by the rotary-preventing and load-carrying means 10. With two grooves 11 or 11a on the outer side of the sleeve 13 of the bone nail, running in the longitudinal direction of the sleeve, said grooves are configured e.g. in line with the lateral opening 14 in the sleeve 13 and diametrically opposite to said lateral opening respectively, such that the front end portion 15a of the pin 15 will protrude from the lateral opening 14 in the sleeve 13 and into surrounding bone tissue in the inner bone fragment 8 in one of two preferred directions when one of the grooves 11 or 11a is correctly located relative to the rotary-preventing and load-carrying means 10.

According to another alternative, not illustrated in the drawings, the sleeve 13 of the bone nail can also be configured with two opposing lateral openings 14 and the pin 15 therein can be configured with two front end portions 15a which during displacement of the pin and simultaneous deformation of said front end portions are driven out of the sleeve via the lateral openings therein for engagement in the surrounding bone tissue in the inner bone fragment 8. With such an embodiment of the bone nail, the sleeve 13 is also configured with two on the outside of said bone nail in the longitudinal direction of the sleeve extending and at a 90° angle relative to the lateral openings 14 located grooves 11 or 11a for engagement in one of the grooves by the rotary-preventing and load-carrying means 10. This means that when the pin 15 has two front end portions 15a for engagement in bone tissue, these front end portions will protrude in diametrically opposite directions and with a 90° displacement relative to a pin with only one front end portion.

It is within the scope of the present invention of course possible to configure the proximal fixing means 3, irrespective of whether it is a bone screw or a bone nail, with grooves 11 for a rotary-preventing and load-carrying means 10 in the form of a peg 10a as well as with grooves 11a for a rotary-preventing and load-carrying means in the form of a screw 10b.

The surgical procedure for implanting the device according to the present invention can be carried through by means of several different techniques and so called "target devices" for correct optimum location and provision of the holes for the various fixing means and is therefore not described in detail here. An important difference which should be mentioned is however that since a locking plate with a sleeve with rotary-preventing means no longer is needed, the proximal fixing means need no longer be positioned first and the sleeve on the locking plate then be threaded onto the proximal portions of the proximal fixing means, including the second fixing portion thereof for cooperation with the locking plate, but instead the locking plate can be positioned first by inserting it into the wound or incision provided for the operation, moving tissues at the bone fracture aside and fitting the locking plate optimally against the outer bone fragment, whereupon the distal and proximal fixing means are inserted through the holes therefor in the locking plate. By positioning the locking plate before the fixing means and since it at a suitable location and orientation of the holes in the locking plate is possible to provide said fixing means and the rotary-preventing and load-carrying means by means of a suitable tool from substantially the same point from the insertion side of the locking plate, the length of the operation wound or incision can be minimized.

It is obvious to a skilled person to modify the device according to the present invention within the scope of the subsequent claims without departing from the idea and purpose of the invention. Thus, the locking plate, the distal fixing means, the proximal fixing means and the rotary-preventing and load-carrying means can all be configured in other ways than what appears from the above description. The number of holes in the locking plate for the various means may e.g. vary and so may the location thereof. If the locking plate has lateral plates, each lateral plate may be configured with at least one hole for a distal fixing means, with advantage two or three holes depending on the length of the lateral plate. The number of distal fixing means may vary correspondingly. The distal fixing means may be of another type than cortical bone screws, the proximal fixing means may be of another type than a bone screw (lag screw) or bone nail of the abovementioned configuration and the rotary-preventing and load-carrying means may be of another type than the abovementioned peg or screw. The material of which said components are made may also vary, i.e. may consist of a suitable metal, metal alloy, plastic or composite or any other combination of materials.

The invention claimed is:

1. Device for fixation of bone fragments at proximal thigh-bone or femoral fractures, said device comprising:
   a locking plate (1) for fixation on the outside of an outer bone fragment (4), said locking plate having a distal portion (1a) with at least one first hole (6), which extends through the locking plate, for a distal fixing means (2) and a proximal portion (1b) with a second hole (7), which extends through the locking plate, for a proximal fixing means (3),
   at least one distal fixing means (2) which is configured for insertion and fixation of the fixing means in said at least one first hole (6) in the distal portion (1a) of the locking plate (1) and fixation of the fixing means in the outer bone fragment, and
   a proximal fixing means (3) which is configured with a first fixing portion (3a) for fixation of the fixing means in an inner bone fragment (8), a second fixing portion (3b) for insertion of the fixing means in said second hole (7) in the proximal portion (1b) of the locking plate (1) for connection of the fixation means to the locking plate for primary compression of the outer and inner bone fragments (4, 8), and a middle portion (3c) which is situated between the first and second fixing portions and configured to extend through the outer bone fragment (4) and to permit, during secondary compression of the outer and inner bone fragments, displacement of the outer bone fragment and the proximal fixing means relative to each other, whereby the connection of the fixing means to the locking plate for achieving primary compression ceases, wherein the locking plate (1) is configured also with a third hole (9) which is located between said at least one first hole (6) in the distal portion (1a) of the locking plate and said second hole (7) in the proximal portion (1b) of the locking plate, the third hole (9) extending through the locking plate (1) at an angle, seen in the cross direction of the locking plate, relative to said second hole (7) in the locking plate (1) such that the third hole does not extend parallel to the second hole, and that the device further comprises a rotary-preventing and load-carrying means (10) which is configured for insertion and fixation in said third hole (9) in the locking plate (1) and engagement distally in a longitudinal groove (11) in the proximal fixing means (3) for preventing rotation of the proximal fixing means but permitting displacement thereof in its longitudinal direction relative to the rotary-preventing and load-carrying means during secondary compression of the outer and inner bone fragments (4, 8), and by means of said distal engagement of the proximal fixing means facilitate for the proximal fixing means to carry loading forces acting on the inner bone fragment (8).

2. Device according to claim 1, wherein the rotary-preventing and load-carrying means (10) is configured as a rod (10a) with a threaded rear end portion (10aa) for fixation in the third hole (9) in the locking plate (1).

3. Device according to claim 2, wherein the front end portion (10ab) of the rod (10a) is conically shaped for engagement into the longitudinal groove (11) in the proximal fixing means (3).

4. Device according to claim 3, wherein the conically shaped surface of the front end portion (10ab) of the rod (10a) is configured such that the part thereof engaging the groove (11) extends in parallel with the surface of said groove.

5. Device according to claim 3, wherein the groove (11) in the proximal fixing means (3) is configured to extend, from the second fixing portion (3b) of the proximal fixing means (3), along at least a part of the middle portion (3c) of said proximal fixing means.

6. Device according to claim 1, wherein the second hole (7) in the proximal portion (1b) of the locking plate (1) and the third hole (9) for the rotary-preventing and load-carrying means (10) in the locking plate are provided in one and the same plane seen in the longitudinal direction of the locking plate.

7. Device according to claim 6, wherein said plane extends, seen in the longitudinal direction of the locking plate, substantially straight through the locking plate between the insertion side (1c) for the fixing means (2, 3) and for the rotary-preventing and load-carrying means (10) and the side (1d) of the locking plate engaging the outer bone fragment (4).

8. Device according to claim 1, wherein the third hole (9) for the rotary-preventing and load-carrying means (10) in the locking plate (1) is, seen in the cross direction of said locking plate, configured extending at an angle relative to said at least one first hole (6) for a distal fixing means (2) in the distal portion (1a) of said locking plate.

9. Device according to claim 8, wherein the locking plate (1) in the distal portion (1a) thereof is configured with two or more first holes (6) for distal fixing means (2), wherein said first holes (6) for distal fixing means (2) in the distal portion (1a) of the locking plate (1) extend, seen in the cross direction of the locking plate, substantially in parallel with each other and at an angle relative to the second hole (7) for the proximal fixing means (7) in the proximal portion (1b) of the locking plate and relative to the third hole (9) for the rotary-preventing and load-carrying means (10) in the locking plate.

10. Device according to claim 8, wherein the locking plate (1) in the distal portion (1a) thereof is configured with two or more first holes (6) for distal fixing means (2), wherein said first holes (6) for distal fixing means (2) in the distal portion (1a) of the locking plate (1) extend, seen in the cross direction of the locking plate, at an angle relative to each other and at an angle relative to the second hole (7) for the proximal fixing means (3) in the proximal portion (1b) of the locking plate and relative to the third hole (9) for the rotary-preventing and load-carrying means (10) in the locking plate.

11. Device according to claim 10, wherein the first holes (6) in the distal portion (1a) of the locking plate (1), the second hole (7) in the proximal portion (1b) of the locking plate and the third hole (9) in the locking plate extend all, seen in the cross direction of the locking plate, obliquely through said locking plate such that distal fixing means (2) which have been inserted into said first holes run in the direction of insertion away from the proximal fixing means (3) which has been inserted into said second hole and away from the rotary-preventing and load-carrying means (10) which has been inserted into said third hole.

12. Device according to claim 11, wherein the first holes (6) in the distal portion (1a) of the locking plate (1), the second hole (7) in the proximal portion (1b) of the locking plate and the third hole (9) in the locking plate extend all, seen in the cross direction of the locking plate, obliquely through said locking plate such that distal fixing means (2) which have been inserted into said first holes are located in planes which on the insertion side (1c) of the locking plate cross each other and cross the planes in which the proximal fixing means (3) which has been inserted into said second hole and the rotary-preventing and load-carrying means (10) which has been inserted into said third hole are located.

13. Device according to claim 9, wherein said first holes (6) for distal fixing means (2) in the distal portion (1a) of the locking plate (1) extend, seen in the longitudinal direction of the locking plate, at an angle relative to each other and at an angle relative to a plane through the second hole (7) for the proximal fixing means (7) in the proximal portion (1b) of the locking plate and through the third hole (9) for the rotary-preventing and load-carrying means (10) in the locking plate.

14. Device according to claim 13, wherein said first holes (6) for distal fixing means (2) in the distal portion (1a) of the locking plate (1) extend, seen in the longitudinal direction of the locking plate, obliquely through the locking plate such that distal fixing means (2) which have been inserted into said first holes are located in planes which on the insertion side (1c) of the locking plate cross each other and cross the plane in which the proximal fixing means (3) which has been inserted into said second hole (7) in the proximal portion (1b) of the locking plate and the rotary-preventing and load-carrying means (10) which has been inserted into said third hole (9) are located.

15. Device according to claim 1, wherein the second fixing portion (3b) of the proximal fixing means (3) is configured with a threaded recess (3ba) for a locking and compression screw (12) for locking said proximal fixing means to the locking plate (1).

16. Device according to claim 1, wherein proximally of the proximal portion (1b) of the locking plate (1), said locking plate is provided with a lateral support (1e).

17. Device according to claim 16, wherein the lateral support (1e) is configured in one piece with the locking plate (1).

18. Device according to claim 1, wherein the proximal fixing means (3) is configured as a bone screw, the bone screw is on the outer side thereof provided with at least one groove (11 and/or 11a) which runs in the longitudinal direction of the bone screw for engagement in the groove by the rotary-preventing and load-carrying means (10).

19. Device according to claim 1, wherein the proximal fixing means (3) is configured as a bone nail, said bone nail comprising a sleeve (13) with at least one lateral opening

(14) in a front end portion (13a) of the sleeve and at least one pin (15) which is displaceably mounted inside said sleeve and has at least one front end portion (15a) which defines the first fixing portion (3a) of the proximal fixing means and which during displacement of the pin and simultaneous deformation of said at least one front end portion is driven out of the sleeve via the lateral opening therein for engagement in the surrounding bone tissue in the inner bone fragment (8), wherein the sleeve (13) of the bone nail is on the outer side thereof provided with at least one groove (11 and/or 11a) which runs in the longitudinal direction of the sleeve for engagement in the groove by the rotary-preventing and load-carrying means (10).

20. Device according to claim 19, wherein the sleeve (13) of the bone nail is on the outer side thereof, in line with the lateral opening (14), provided with one groove (11 or 11a) which runs in the longitudinal direction of the sleeve for engagement in the groove by the rotary preventing and load-carrying means (10).

* * * * *